US00PP32188P2

(12) United States Plant Patent
Cain

(10) Patent No.: US PP32,188 P2
(45) Date of Patent: Sep. 15, 2020

(54) SWEET CHERRY TREE NAMED 'IFG CHER-NINE'

(50) Latin Name: *Prunus avium*
Varietal Denomination: IFG Cher-nine

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 16/602,626

(22) Filed: Nov. 14, 2019

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

*Primary Examiner* — Kent L Bell

(57) ABSTRACT

This invention is a new and distinct sweet cherry tree denominated 'IFG Cher-nine'. The new sweet cherry tree is characterized by producing early ripening medium size dark red fruits having a reniform shape. Fruits ripen early and are very firm, with medium acid fruit with a good cherry flavor. Fruits are tolerant of rain induced cracking. The tree has a low chilling requirement of about 300 to 400 hours. It produces few doubled and spurred fruits.

1 Drawing Sheet

Latin name of the genus and species claimed: *Prunus avium.*

Variety denomination: 'IFG Cher-nine'.

BACKGROUND OF THE INVENTION

The new and distinct sweet cherry tree described and claimed herein originated from open pollinated seeds of fruits of an early ripening unidentified female parent located in Bakersfield, Kern County, Calif. collected in May 2001. The male parent is unknown. The seeds were stratified, germinated and the resulting 540 seedlings were planted in the field near Delano, Kern County, Calif. in April 2002. The present variety of sweet cherry tree was selected as a single plant in May 2005 and was first asexually propagated in May 2007 by grafting onto *Prunus mahalab* rootstock. This propagule was found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that sweet cherries are available. The sweet cherry breeding program focuses on developing types of cherries that will grow in regions with low winter chilling and high summer temperatures so that the fruit will ripen before fruit in traditional growing regions.

The new sweet cherry tree 'IFG Cher-nine' is characterized by producing early ripening medium size dark red fruits having a reniform shape. The fruits of 'IFG Cher-nine' ripen early and are very firm, with medium acid fruit with a good cherry flavor. Fruits are tolerant of rain induced cracking. The tree has a low chilling requirement of about 300 to 400 hours. It produces few doubled and spurred fruits. Fruits of 'IFG Cher-nine' have medium long, thick stems that remain attached and stay green during storage and shipping.

In comparison to its female parent, the present variety has larger fruits with shorter thicker stems.

In comparison to the 'Brooks' variety (U.S. Plant Pat. No. 6,676), which is a major variety grown in warm regions, the present variety ripens about three to five days earlier and has more desirable darker red skin and flesh. It also has fewer undesirable doubled and spurred fruits as compared to 'Brooks' and has superior storage characteristics.

In comparison to 'IFG Cher-three' (U.S. Plant Pat. No. 30,011), 'IFG Cher-nine' is similar in appearance, fruit size and fruit firmness. It differs from 'IFG Cher-three' by blooming on average one or two days later and by having the pollen compatibility group of S3S4 compared to S3S6 for 'IFG Cher-three'.

'IFG Cher-nine' is being introduced to provide a pollinator variety for 'IFG Cher-three'. Both have similar chilling requirements, bloom times, ripe dates and fruit characteristics so they can be harvested and marketed together.

BRIEF DESCRIPTION OF THE DRAWING

The accompanying photographic drawing illustrates in full color 'IFG Cher-nine', taken from a 12-year old tree. The photograph was taken outdoors with indirect lighting. The colors are as nearly true as is reasonably possible in a color representation of this type. An actively growing shoot tip can be seen in the center portion of the drawing. Typical mature fruit, fruit in cross section and cleaned and dried fruit pits are displayed in the right portion of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification, subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to 'IFG Cher-nine' plants grown in the vicinity of Delano, Kern County, Calif. during 2017-2019, and is believed to apply to plants of the variety grown under similar conditions of soil and climate elsewhere:

Tree:

General:

*Age*.—12 years old.

*Height*.—About 2.8 M when pruned.

*Width*.—About 3.8 M when pruned.

*Vigor*.—Vigorous.

*Density of foliage*.—Dense.

*Form*.—Upright.

*Branching*.—Strong.

*Root stock*.—*Prunus mahalab*.

*Resistance to*.—Insects: Average typical of *Prunus avium* species. Diseases: Average typical of *Prunus avium* species.

*Chilling requirements*.—Very low to low.

*Graft compatibility*.—Good: produces compatible graft unions with *Prunus avium*, 'Mazzard' seedling (non-patented) and *Prunus mahaleb* seedlings (non-patented).

Trunk:

*Trunk diameter of* 12-*year-old tree,* 30 *cm above the soil line*.—About 33.4 cm.

*Lenticel size*.—Medium.

*Lenticel dimensions*.—Length: About 1.4 cm. Width: About 0.2 cm.

*Lenticel shape*.—Elliptical shape oriented horizontally.

*Lenticel color*.—Grey: 201B.

*Trunk surface texture*.—Medium rough.

*Outer bark color*.—The following colors were observed: Greyed-purple: N186C and N187C.

Branches:

1-year-old wood:

*Vertical top growth length*.—Long: About 106 cm.

*Horizontal growth length*.—Medium: About 56 cm.

*Diameter*.—Vertical growth: About 1.0 cm. Horizontal growth: About 0.5 cm.

*Internode length*.—Medium: About 3.6 cm.

*Number of lenticels*.—Few: About 3 lenticels per linear cm.

*Lenticel size*.—Small.

*Lenticel dimensions*.—Length: About 0.1 cm. Width: About 0.1 cm.

*Lenticel shape*.—Round.

*Bark color*.—The following colors were observed: Greyed-orange: 166A and 166B.

2-year-old wood:

*Length*.—Long: About 55.5 cm.

*Diameter*.—About 1.0 cm.

*Internode length*.—About 3.5 cm.

*Number of lenticels*.—Medium: About 6.

*Lenticel dimensions*.—Length: About 1.3 mm. Width: About 1.0 mm.

*Lenticel shape*.—Elliptical shape oriented horizontally.

*Bark color*.—Greyed-orange: 165A.

Buds:

Vegetative buds:

*Shape*.—Elongated.

*Vegetative bud dimensions*.—Length: About 7.6 mm. Width: About 4.1 mm.

*Bud burst*.—Approximately Feb. 19, 2018.

Flower buds:

*Flower bud dimensions*.—Length: About 8.5 mm. Width: About 4.1 mm.

*Shape*.—Oval.

*Placement*.—At bud positions mostly 1 to 14 on first-year wood.

*Average number of flower buds on first year wood*.—About 13.

*Number of flower buds per spur on second year wood*.—3 to 9. Average: About 5.

*Color*.—Greyed-orange: 165A.

Leaves:

Mature leaves:

*Leaf dimensions*.—Length: About 12.8 cm. Width: About 5.7 cm.

*Leaf shape*.—Ovate: Symmetric on both sides of central axis.

*Shape of tip*.—Acuminate: Broadly.

*Shape of base*.—Attenuate.

*Margin*.—Serrated: regular: rounded.

*Leaf profile*.—Involute.

*Venation*.—Arcuate.

*Vein color*.—The following colors were observed: Yellow-green: 144B and 144C.

Upper surface:

*Upper surface pubescence*.—Very sparse.

*Upper leaf surface color*.—Green: 137A.

*Surface texture*.—Medium.

Lower surface:

*Lower surface pubescence*.—Sparse: only on veins.

*Lower leaf surface color*.—Yellow-green: 147B.

Petiole:

*Petiole dimensions*.—Length: About 4.5 cm. Width: About 0.15 cm.

*Upper surface of petiole color*.—Yellow-green: 146B.

*Lower surface of petiole color*.—Yellow-green: 144B.

*Petiole groove*.—Narrow: Approximately 0.5 mm.

*Petiole pubescence*.—Very sparse to none: On both upper and lower surfaces.

Glands:

*Number of glands*.—2.

*Gland dimensions*.—Length: About 1.5 mm. Width: About 1.2 mm.

*Gland shape*.—Mixture of reniform and globose.

*Gland location*.—On petiole.

*Gland color*.—The following colors were observed: Greyed-red: 178A and 178B and 178C.

*Leaf stipule*.—Present.

Flowers:

*Blooming period*.—Early-season.

*Blooming dates*.—First Bloom: Approximately Mar. 1, 2018. Full Bloom: Approximately Mar. 10, 2018.

*Number of flowers per cluster*.—3 to 5. Average: About 3.5.

*Corolla*.—Composed of unfused petals, slightly overlapping.
*Corolla diameter*.—About 3.3 cm.
*Petal number*.—Most have 5, few have 6 or 8.
*Petal length*.—About 1.6 cm.
*Petal width*.—About 1.6 cm.
*Margin waviness*.—Weak to medium.
*Division of upper margin*.—Notched.
*Color of petal upper surface*.—White: NN155C.
*Color of petal lower surface*.—White: NN155C.
*Peduncle*.—Length: About 1.7 cm. Width: About 1.9 mm.
*Peduncle color*.—Yellow-green: 144C.
*Number of sepals*.—Most have 5, few have 6 or 8.
*Sepal length*.—About 0.8 cm.
*Sepal width*.—About 0.8 cm.
*Sepal shape*.—Elongated ovate.
*Sepal color*.—Inner surface: Yellow-green: 144C. Outer surface: The following colors were observed: Yellow-green:144C and Greyed-red: 181A.
*Filament*.—Length: 0.5 to 1.5 cm. Width: About: 0.9 mm.
*Filament color*.—White: NN155C.
*Anther color*.—Greyed-yellow: 162B.
*Pollen color*.—The following colors were observed: Greyed-yellow: 162A and 162C.
*Pollen production*.—Medium to high.
*Self-compatibility of flowers*.—Self-incompatible.
*Pollen compatibility group*.—S3S4.

Fruit:

General:
*Ripening period*.—Early: Approximately: May 4, 2017.
*Use*.—Fresh market.
*Keeping quality*.—Good.
*% Titratable acidity*.—About 0.93%.
*Refractometer test*.—Soluble solids: Brix: About 17.0.
*Firmtech II* (*g/mm*).—About 288.
*Flavor*.—Good.
*Juice color*.—Greyed-purple: 187A.
*Juice amount*.—Moderately juicy.
*Eating quality*.—Good.

Stem:
*Stem*.—Length: About 3.8 cm. Width: About 1.5 mm.
*Stem color*.—Yellow-green: 146B.
*Stem cavity*.—Medium.
*Stem retention during storage*.—Excellent.
*Stem storage quality*.—Good.

Berry:
*Uniformity of size*.—Uniform.
*Shape*.—Reniform.
*Fruit weight*.—About 7.5 gm.
*Apical diameter*.—About 2.4 cm.
*Diameter transversely across suture*.—About 20.3 mm.
*Diameter at right angle to suture plane*.—About 25.1 mm.
*Suture*.—None.
*Percent of excessively deep or split sutures*.—About 6%.
*Doubles*.—About 2%.

Skin:
*Thickness*.—Average.
*Texture*.—Smooth.
*Skin color*.—Greyed-purple: 187A.
*Tendency to crack*.—Not susceptible.

Flesh:
*Texture*.—Intermediate.
*Color*.—The following colors were observed: Greyed-purple: 187B and 187C.
*Stone cavity color*.—Greyed-purple: 187A.

Stone:
*Shape*.—Ovate.
*Length*.—About 11.2 mm.
*Width across suture*.—About 8.8 mm.
*Width at right angle to suture plane*.—About 5.9 mm.
*Dry stone weight*.—About 0.2 gm.
*Type*.—Clingstone.
*Surface texture*.—Smooth.
*Stone color when dry*.—Orange-white: 159A.
*Tendency to split*.—None.
*Base*.—Rounded.
*Apex*.—Rounded.
*Ventral edge*.—Narrow suture subtended by 2 somewhat prominent ridges converging at base and apex. Suture can protrude slightly beyond the horizontal plane of the base of the stone.
*Dorsal edge*.—Smooth, narrow ridge from base to apex.

What is claimed:

1. A new and distinct variety of sweet cherry tree as herein illustrated and described.

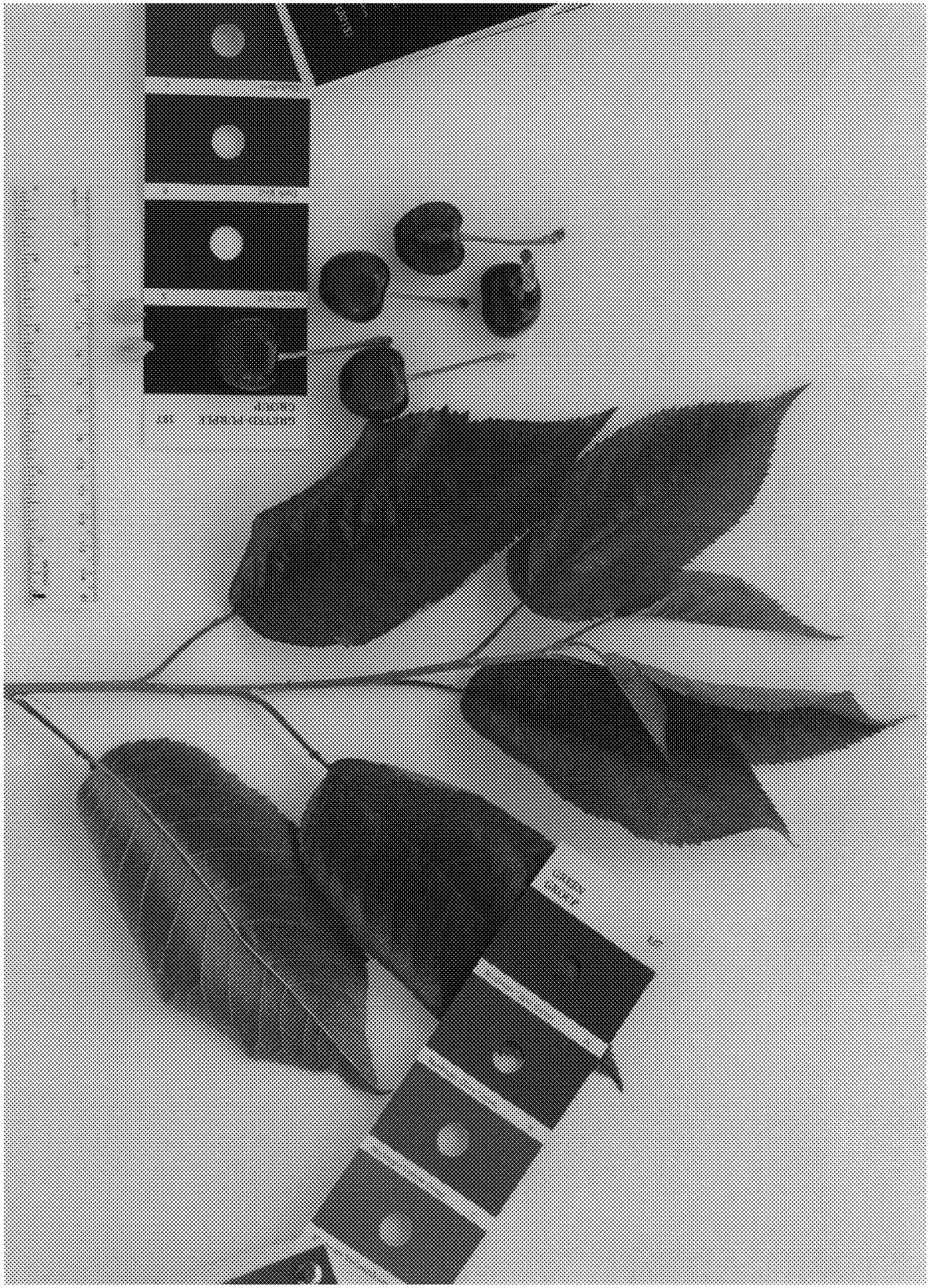

* * * * *